US00PP12062P2

(12) United States Plant Patent
Speichert

(10) Patent No.: US PP12,062 P2
(45) Date of Patent: Aug. 21, 2001

(54) PERSICARIA PLANT NAMED 'RED DRAGON'

(76) Inventor: C. Greg Speichert, P.O. Box 154, St. John, IN (US) 46373

( * ) Notice: Subject to any disclaimer, the term of this patent is extended or adjusted under 35 U.S.C. 154(b) by 0 days.

(21) Appl. No.: 09/391,955

(22) Filed: Sep. 8, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para

(57) ABSTRACT

A new cultivar of Persicaria named 'Red Dragon' that is particularly distinguished in having purple-brown colored spring foliage, red stems and a clump-forming habit of growth.

3 Drawing Sheets

BACKGROUND OF THE INVENTION

The present invention relates to a new and distinct cultivar of *Persicaria microcephela*, herein be referred to as 'Red Dragon'. 'Red Dragon' is unique in that it has purple-brown colored spring foliage, red stems, and is clump-forming.

The new Persicaria was discovered as a naturally occurring mutant seedling that arose in a crop of *Persicaria microphela* (unpatented) that was grown for medicinal purposes in Nanjing, China. The new invention was selected because it is unique in that the spring foliage emerges a deep purple-brown color, the stems are red and the plant exhibits a clump-forming growth habit. *Persicaria microphela* has green foliage throughout the growth season, has green stems and has a stoloniferous growth habit. Although the inventor cannot say with certainty, both the pollen and seed parent are presumed to be *Persicaria microcephela* as no other species of Persicaria were present in the cultivated area where 'Red Dragon' was discovered. There are no cultivars of *Persicaria microphela* currently in commerce.

Asexual reproduction of the new cultivar was first accomplished by taking cuttings in St. John, Ind. on April, 1997 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from the typical form of the species.

1. The emerging foliage of 'Red Dragon' is a deep purple-brown color with a lighter chevron-shaped coloration pattern that varies from a gray-brown color to a mint green. The foliage changes to a silvery-purple color and finally to green as the season progresses and the foliage matures. The species is green with a lighter colored green chevron throughout the growing season.

2. The stems of 'Red Dragon' are red throughout the growing season. The stems of the species are green.

3. 'Red Dragon' increases in a clump-forming manner, whereas the species is stoloniferous.

4. Clusters of white corymb-like flowers appear in late summer.

BOTANICAL DESCRIPTION OF THE PLANT

Figure 1:
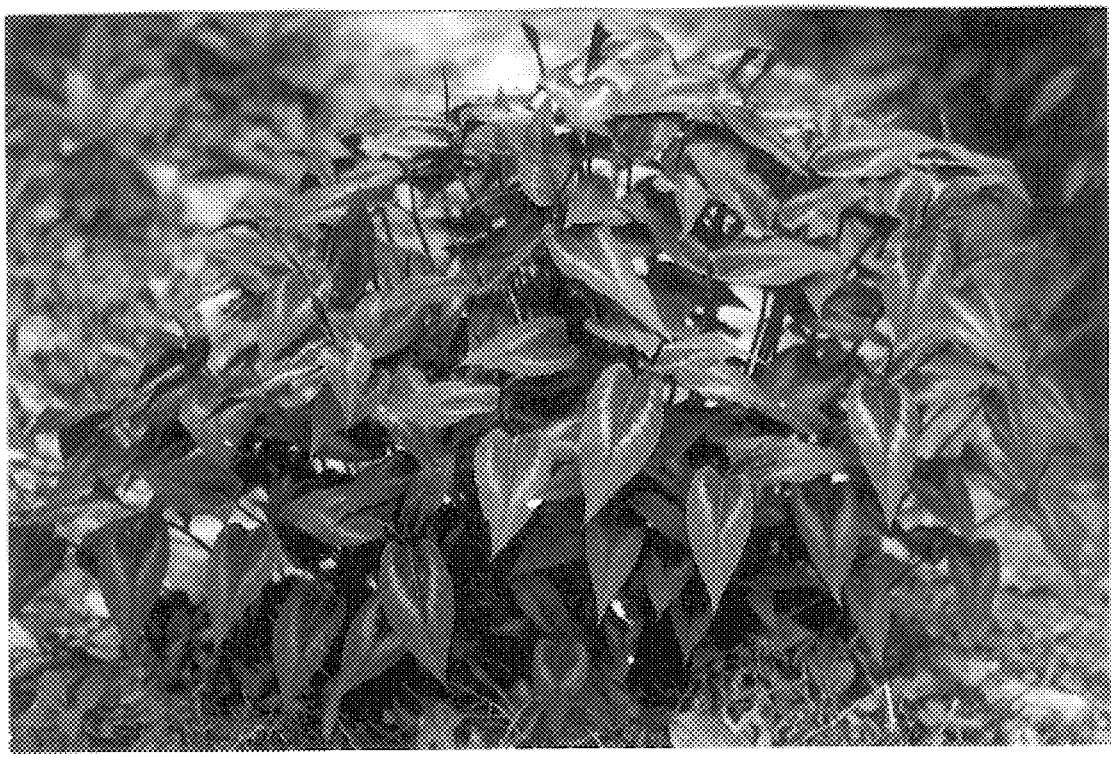
FIG. 1 is a photograph of Persicaria 'Red Dragon' as grown in a garden in Indiana in May. The clump forming habit is depicted as is the silvery-purple foliage color observed in late spring to early summer.
Figure 2:
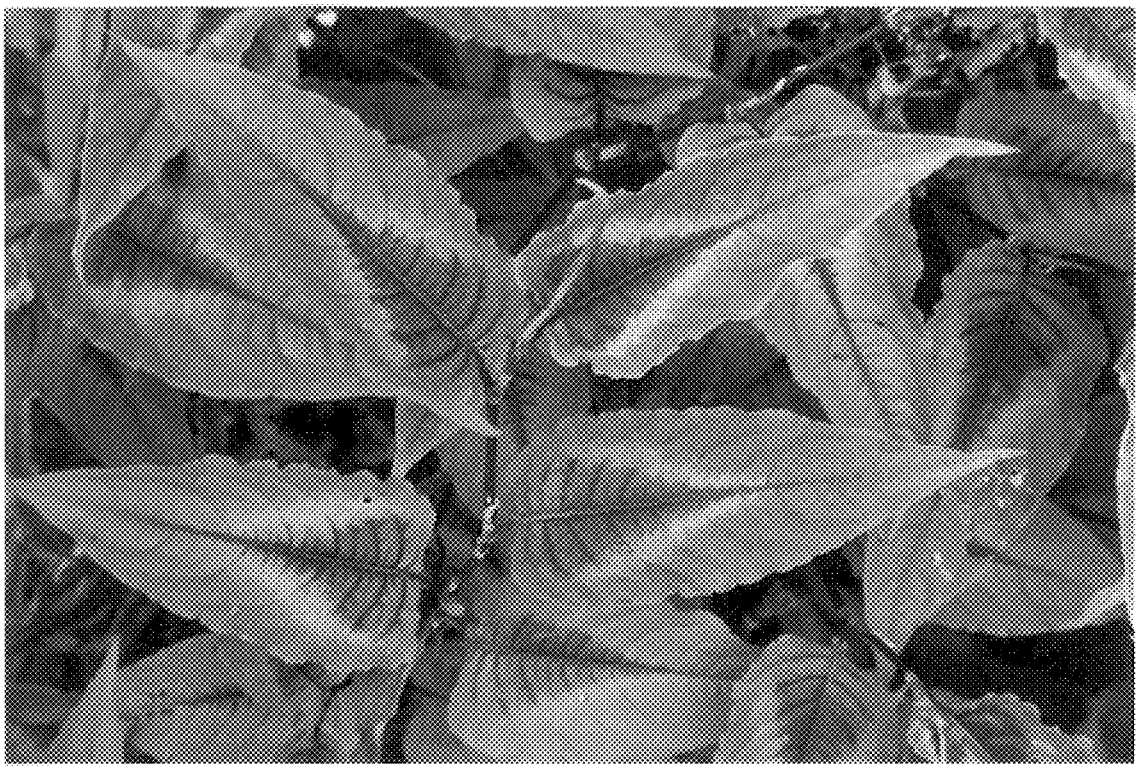
FIG. 2 is a photograph of 'Red Dragon' taken in July and shows the foliage color and retention of the red stems in summer.
Figure 3:
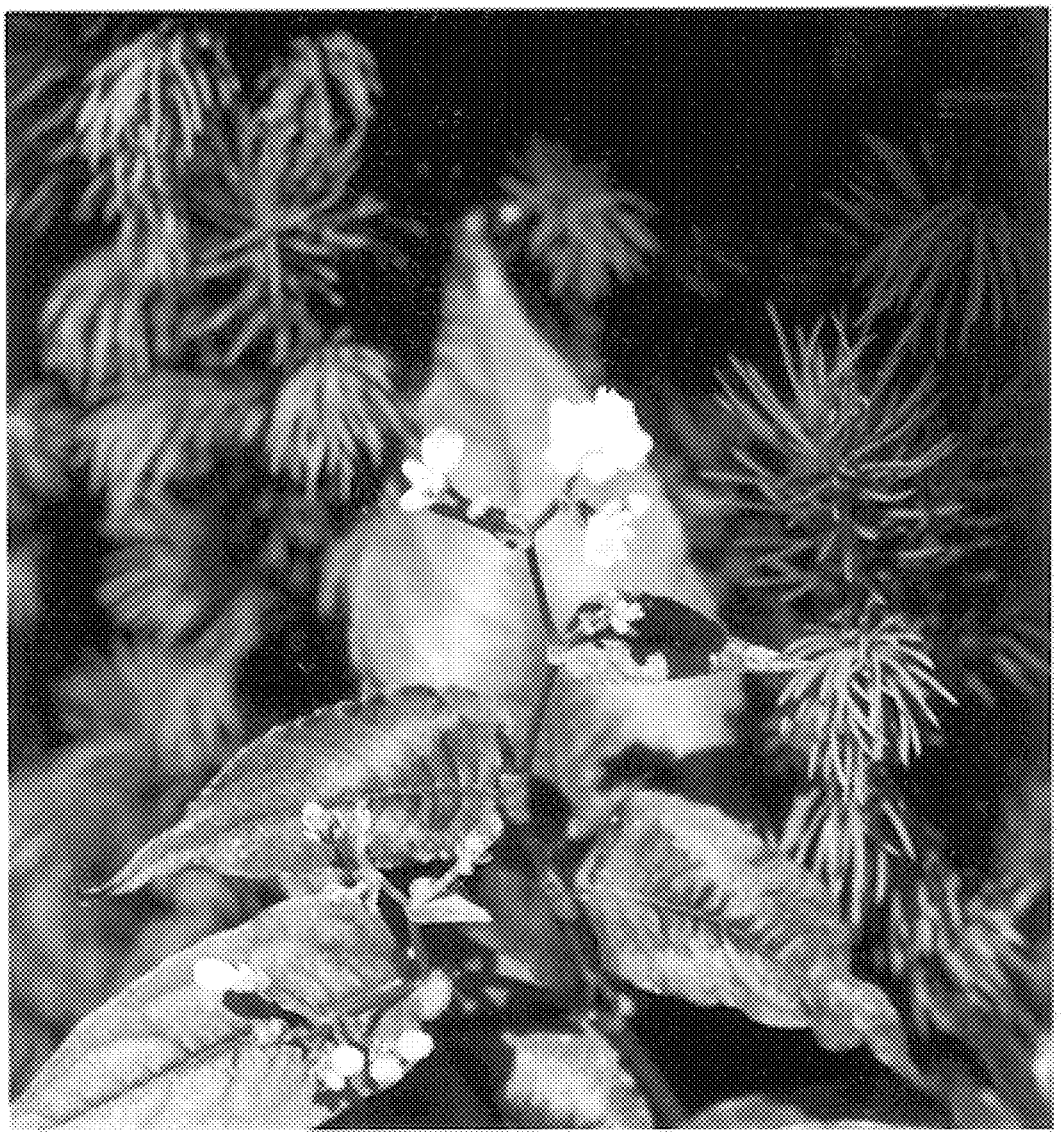
FIG. 3 is a photograph of 'Red Dragon' taken in late summer when in bloom. The color of these photographs are as accurate as possible by conventional photography.

The following is a detailed description of a one year old plant of the new cultivar as grown in a one-gallon container under outdoor conditions in Minnesota: Phenotypic differences may be observed with variations in environmental, climatic, and cultural conditions. The color determination is in accordance with the R.H.S. Colour Chart of The Royal Horticultural Society, London, England, except where general color terms of ordinary dictionary significance are used.

Botanical classification: 'Red Dragon' is a cultivar of *Persicaria microcephala.*

Parentage: Discovered as a naturally occurring mutant seedling of *Persicaria microcephala;* both seed and pollen parents are presumed to be *Persicaria microcephala.*

Plant description:

- *Blooming period.*—Short day photoperiodic, blooms July–August.
- *Plant growth.*—Rounded mound, clump-forming.
- *Height and spread.*—58 to 75 cm in height, 75 to 90 cm in width.
- *Hardiness.*—Zone 5 (possibly 4).
- *Type.*—Perennial.
- *Root description.*—Fibrous.
- *Propagation.*—Terminal stem cuttings.
- *Culture.*—Sunny location in well-drained, moderately fertile soils.
- *Disease, insect, and drought resistance/susceptibility.*—No known resistance or susceptibility as compared to the species. Not drought tolerant; moisture retentive soil is required for best garden performance and foliage coloration.

Stems:

*Shape.*—Round.

*Size.*—2–5 cm in diameter.

*Color.*—84A.

*Surface.*—Glabrous.

*Internode length.*—1.5–5 cm (average 3 cm).

Leaves:

*Shape.*—Ovate-lanceolate.

*Division.*—Simple.

*Base.*—Truncate to auriculate.

*Apex.*—Acuminate.

*Venation.*—Pinnate, mid-vein prominent (upper color 187B, lower color 182A–C).

*Margins.*—Entire (slightly crisped and crenated).

*Attachment.*—Petiolate.

*Arrangement.*—Opposite.

*Surface.*—Lower is glabrous, upper has short hairs and is dull in appearance.

*Size.*—Up to 1.8 cm wide and 4 cm long.

*Petioles.*—6–10 mm in length, 1.3–5 mm in width, quandrangular, color is 184A.

*Color.*—Emerging foliage; Upper: purple-brown (intermediate between 200A and 187A) with a gray-brown (199B) to mint green (147C) chevron, Lower: same coloration as upper with a flush of 147C.

*Mid summer foliage* (*upper and lower*).—Silvery-purple with outer portion intermediate between 201C and 202C and basal portion intermediate between 201B and 202B, chevron coloration as described for emerging foliage.

*Late summer foliage.*—Upper: Green (146A) with a lighter green (147C) chevron, a thin red margin (182A) and on some leaves there is a burgundy basal coloration (187A), Lower: 146B.

Flowers:

*Type.*—Terminal, corymb-like, campanulate.

*Corymb size.*—3 cm in height and width.

*Peduncles.*—Primary 3–3.5 mm in length, secondary 1–2.5 mm in length.

*Number.*—8–20 florets corymb-like cluster.

*Tepals.*—6, deltoid in shape, lustrous in texture, 3 mm in length, 2 mm in width, white in color (whiter than 155D).

*Stamens.*— 8.

*Pistils.*—Non-existent (dioecious species).

Fruits/seed: Not observed, staminate plant.

I claim:

1. A new and distinct cultivar of Persicaria plant named 'Red Dragon' substantially as herein illustrated and described.

* * * * *